United States Patent [19]
Grasshoff

[11] Patent Number: 5,583,462
[45] Date of Patent: Dec. 10, 1996

[54] METHOD AND APPARATUS FOR MULTIPLEXING DEVICES HAVING LONG THERMAL TIME CONSTANTS

[75] Inventor: Eric Grasshoff, San Diego, Calif.

[73] Assignee: Unifet Incorporated, San Diego, Calif.

[21] Appl. No.: 434,128

[22] Filed: May 3, 1995

Related U.S. Application Data

[63] Continuation of Ser. No. 53,521, Apr. 26, 1993, abandoned.

[51] Int. Cl.$^6$ .......................... H03H 11/26; G11C 27/02; G01N 27/26
[52] U.S. Cl. .......................... 327/262; 327/91; 204/408; 204/416
[58] Field of Search .................................. 307/352, 353, 307/243, 591; 328/104; 204/406, 408, 416; 327/83, 262, 91

[56] References Cited

U.S. PATENT DOCUMENTS

| | | | |
|---|---|---|---|
| 4,010,385 | 3/1977 | Krol | 307/243 |
| 4,701,253 | 10/1987 | Ligtenberg | 204/416 |
| 5,111,072 | 5/1992 | Seidel | 307/353 |
| 5,247,210 | 9/1993 | Swanson | 307/352 |
| 5,281,860 | 1/1994 | Krenik | 307/353 |

OTHER PUBLICATIONS

Bergveld, P., et al., Analytical and Biomedical Applications of Ion–Selective Field–Effect Transistors, vol. XXIII, pp. 108–112, 1988.

Bergveld, Piet, Design Considerations for an Isfet Multiplexer and Amplifier, Sensors and Actuators, 5 (1984), pp. 13–20.

Valdes–Perezgasga and Covington, "Multisensor operation of ion–sensitive field–effect transistors in the constant current mode," *Sensors and Actuators B*, 6 (1992) 219–222.

*Primary Examiner*—William L. Sikes
*Assistant Examiner*—Tiep H. Nguyen
*Attorney, Agent, or Firm*—Fish & Richardson P.C.

[57] ABSTRACT

A method and apparatus for rapidly measuring chemical properties of a solution using a plurality of devices having relatively long thermal time constants selectively coupled to a control means. Current $I_d$ flows through only one device at a time. A timing logic control circuit controls the timing of the drain switch and, if present, the reference switch. The output of the multiplexing circuit is sampled a precise amount of time after each device begins conducting current. The temperature at the sample time is a constant. The characteristics of the solution in which the device is immersed is the only variable in the operation of the device (i.e., $I_d$, and $V_{ds}$ are held constant). By sampling the output a predetermined amount of time after the device has been turned on, the temperature rise is controlled. In this way, the effects of temperature rise due to conduction on the device are constant at each sample time and can be neglected, and the characteristics of the solution can be precisely determined without waiting for the temperature to stabilize.

17 Claims, 5 Drawing Sheets

METHOD AND APPARATUS FOR MULTIPLEXING DEVICES HAVING LONG THERMAL TIME CONSTANTS

This is a continuation of application Ser. No. 08/053,521, filed Apr. 26, 1993, now abandoned.

BACKGROUND OF THE INVENTION

1. Field of the Invention

This invention relates to electronic sensors, and more particularly to a method and apparatus for rapidly determining chemical properties of a solution using a plurality of ion-sensitive field effect transistors.

2. Description of Related Art

It is known to use ion-sensitive field effect transistors (ISFETs) to detect and measure chemical properties, such as ion activity, within a solution, such as blood. Use of ISFETs for detecting and measuring chemical properties of blood can, among other things, enhance a physician's ability to provide efficient care to a patient by providing essentially continuous information about the patient's blood chemistry.

U.S. Pat. No. 4,020,830 to Johnson et al., discloses an ISFET capable of detecting and measuring concentrations of ions, such as $H^+$, $Na^+$, $K^+$, or $Ca^{++}$. An ISFET operates in a manner that is similar to the operation of a standard metal oxide semiconductor field effect transistor (MOSFET) device. For example, in a standard N-channel MOSFET, two spaced apart diffusion regions having an N-type doping (one doped region being referred to as the source and the other as the drain) are located in the upper surface of a substrate. The region of the substrate that separates the source and the drain is referred to as the channel. Typically, an electrical insulating material is grown over the channel. An electrically conductive material is deposited on each of the N-type diffusion regions and on the insulating material which covers the channel, to form electrical contacts to the source and drain. A gap between the two regions of deposited electrically conductive material forms a "gate". The result is a device in which current flowing from one diffusion region to the other when an electrical potential is applied between the two diffusion regions, can be controlled by varying the voltage applied to the gate contact.

In the case of an ISFET, the structure is similar, except that a membrane which is adapted to selectively interact with a particular ion is deposited over the insulating material that covers the gate region of the substrate. The entire structure is then sealed in a material that is impervious to those solutions in which the ISFET is intended to operate, leaving only a portion of the membrane exposed. The device may then be immersed in a solution. A reference electrode coupled to the ISFET is placed into the solution and an electrical potential is applied such that ions in the solution interact with the ion-selective membrane. This creates an electrochemical voltage at the gate of the device, and an electric field in the conduction channel of the substrate. The strength of the electric field is dependent upon the ion concentration and the voltage applied to the reference electrode, and varies the conduction of electrical current from the source to the drain (i.e., drain current).

ISFETs are typically coupled to an amplifier circuit. Typically, the amplifier circuit acts as an electrical buffer between the ISFET and an output device, and translates the strength of the ion-induced electric field in the channel of the ISFET into an output (either a voltage or current). FIGS. 1A, 1B, and 1C are examples of three amplifier circuits used with ISFETs. The amplifiers of FIGS. 1A and 1B are common gate circuits.

The amplifier of FIG. 1C is a common drain circuit. Variations in the operating point of the ISFET 101 (i.e., the drain current, $I_d$, the drain-to-source voltage, $V_{ds}$, and the temperature of the ISFET 101) can introduce errors when translating the ion-induced electric field at the gate of the ISFET 101 into an output that is proportional to the properties of a solution. Therefore, it is desirable to hold the operating point constant. The circuit of FIG. 1C maintains a constant $I_d$ and $V_{ds}$ with changes in the properties of the solution in which the ISFET 101 is immersed. In the circuit of FIG. 1A, $V_{ds}$ varies as a function of the characteristics of the solution. In the circuit of FIG. 1B, $I_D$ varies as a function of the characteristics of the solution. Thus, because the amplifier of FIG. 1C operates with the least variation in the operating point, it is superior for use with an ISFET 101. However, variations in temperature still cause a shift in the operating point of an ISFET 101.

Frequently, it is desirable to measure more than one chemical property at a time, or to measure the same chemical property using a number of spaced apart ISFETs in the same solution or in different solutions which are electrically connected. As is the case in many data acquisition systems, it is desirable to use a single amplifier circuit which is selectively coupled (i.e., multiplexed) to each ISFET when a plurality of ISFETs are to be used in a system. A simple means for multiplexing ISFETs is to connect each ISFET to the data acquisition system one at a time, having all but the one disconnected. When an ISFET is disconnected, no current flows through the ISFET and the ISFET can be said to be "off".

However, when an ISFET is coupled to a data acquisition system and begins conducting electrical current $I_d$ (i.e., the ISFET is "on"), the ISFET heats due to power dissipated in the ISFET (i.e., the voltage applied between the drain and the source of the ISFET $V_{ds}$ multiplied by the current that flows between the drain and the source of the ISFET $I_d$). This increase in temperature shifts the operating point, and thus alters the relationship between the electrochemical voltage at the gate $V_g$, the drain-to-source voltage $V_{ds}$, and the drain current $I_d$, making it difficult to determine the chemical properties of the solution until the temperature stabilizes. Once the temperature of the ISFET has stabilized, the output can be calibrated. However, due to the exponential response of the temperature stabilization curve, it may be several minutes before the temperature of the ISFET settles to a drift rate small enough to yield an accurate value. This means that each time a different ISFET is switched on (i.e., coupled to an amplifier circuit), that ISFET will require several minutes to "warm up". When a large number of ISFETs are being multiplexed, the time between each consecutive reading of a particular ISFET is equal to the number of ISFETs to be read multiplied by the amount of time required for each to reach a stable temperature. In many measurement applications it is unacceptable to wait for long periods for the results of the measurement.

One way to increase the rate at which multiplexed ISFETs can be read is presented in an article by Piet Bergveld, entitled "Design Considerations for an ISFET Multiplexer and Amplifier". Bergveld proposed maintaining current $I_d$ through each ISFET except for brief time periods during which another ISFET is being read. Each ISFET can be read rapidly if the temperature remains relatively stable. The timing of the Bergveld circuit is such that each ISFET is conducting current for a relatively long period with respect to the time that each ISFET is not conducting. Therefore, when an ISFET is to be read, it is at, or very close to, a stable temperature. FIG. 2 is an electrical schematic diagram of the Bergveld circuit 200.

This solution is practical for amplifiers that operate in the common gate configuration of FIGS. 1A, or 1B. However, the Bergveld circuit 200 precludes the use of the superior common drain amplifier configuration of FIG. 1C, because in a common drain configuration, the ISFET gate is in the amplifier feedback loop. Therefore, it would be necessary to isolate the gate 208a, 208b of each ISFET 201a, 201b from the gate 208a, 208b of each other ISFET 201a, 201b when the ISFET 201a, 201b is turned on (i.e., conducting current $I_d$) so that the current through each ISFET 201a, 201b can be maintained at the proper operating value. This isolation is impossible in the common drain configuration, since the gates of all ISFETs are commoned by the conductivity of the solution. The Bergveld circuit also necessitates the mutual isolation of all ISFET source connections, which is disadvantageous for production of ISFETs.

Therefore, there remains a need for a method and apparatus for ISFET multiplexing which takes advantage of the benefits of a common drain amplifier configuration, while allowing rapid determination of the character of the solution being measured. The following method and apparatus provides such an ISFET multiplexing circuit.

SUMMARY OF THE INVENTION

The present invention overcomes a problem caused by the long turn-on thermal time constant of ISFETs, while permitting the use of a common drain amplifier configuration, or common sources, in a multiplexed ISFET circuit. The drain current, $I_d$ and the drain-to-source voltage, $V_{ds}$ are held constant by the control means, leaving temperature as the only variable which must be compensated for when interpreting the output.

In accordance with the preferred embodiment of the present invention, each ISFET is to be selectively coupled (multiplexed) to a drain voltage supply $V_d$ by a drain switch. Only one ISFET is connected to the drain voltage supply at any one time. Therefore, current $I_d$ flows through only one ISFET at a time. If each ISFET is immersed in the same solution, a single reference electrode can be used for all ISFETs. In cases in which more than one reference electrode is desirable, a reference switch is provided to selectively couple the operational amplifier to a separate reference electrode associated with the active ISFET.

A timing logic control circuit controls the timing of the drain switch and, if present, the reference switch. The output of the multiplexing circuit is sampled a precise amount of time after each ISFET begins conducting current. A gating signal, transmitted from the timing logic control circuit to the sample circuit, controls when the output is to be sampled.

The invention is premised on the observation that the heating of an ISFET follows a repeatable temperature rise curve (temperature vs. time, with a constant drain current $I_d$ and constant drain source voltage, $V_{ds}$). With $I_d$ and $V_{ds}$ held constant, the temperature rise curve depends only on the physical characteristics of the device, such as the size, doping, sealing material, etc. Therefore, if the amount of time an ISFET has been conducting before reading the output of the ISFET is a constant, and the temperature of the ISFET at the start of each conduction period is a constant, the temperature at the sample time will also be constant. The temperature of the ISFET and the characteristics of the solution in which the ISFET is immersed are then the only variables in the operation of the ISFET (i.e., $I_d$ and $V_{ds}$ are held constant). By sampling the output of the operational amplifier a predetermined amount of time after the drain of an ISFET has been coupled to the drain voltage supply, the temperature rise is controlled. In addition, the exact amount of time that the ISFET is not conducting is also precisely controlled, thus the temperature at the beginning of a conduction period is controlled. In this way, the effects of variations in the temperature of each ISFET due to multiplexing are constant at each sample time and do not contribute to the system error. Thus, the characteristics of the solution can be precisely measured without waiting for the temperature to stabilize and each ISFET of a plurality of multiplexed ISFETS may be accurately sampled at a more rapid rate, even though each ISFET is operating in a common drain configuration.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWINGS

Like reference numbers and designations in the various drawings refer to like elements.

DETAILED DESCRIPTION OF THE INVENTION

Throughout this description, the preferred embodiment and examples shown should be considered as exemplars, rather than as limitations on the present invention.

CIRCUIT DESCRIPTION

Figure 1A:
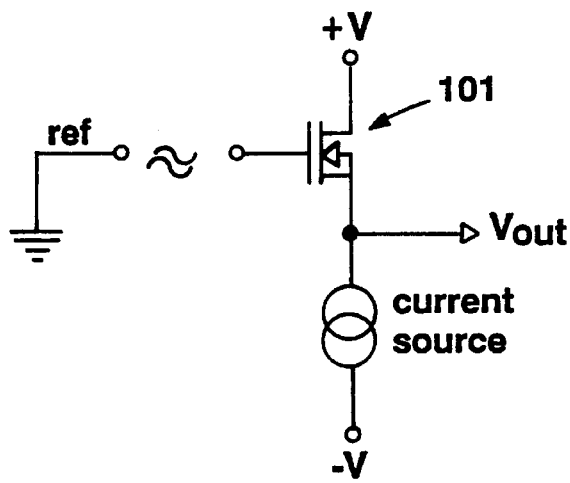
FIG. 1A is an electrical schematic diagram of a prior art common gate amplifier circuit in which the drain current of an ISFET is held constant over time.
Figure 1B:
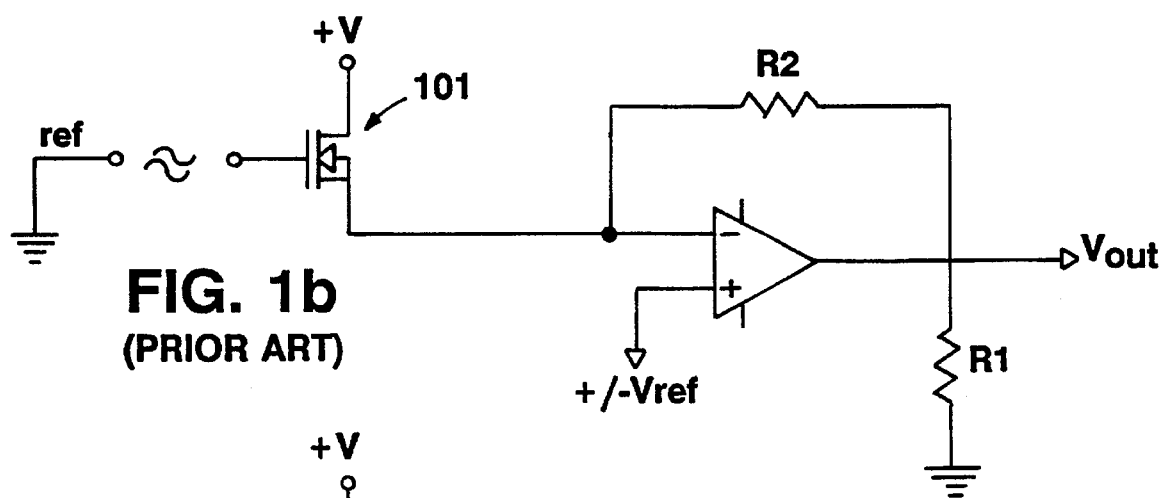
FIG. 1B is an electrical schematic diagram of a prior art common gate amplifier circuit in which the voltage between the drain and source is held constant over time.
Figure 1C:
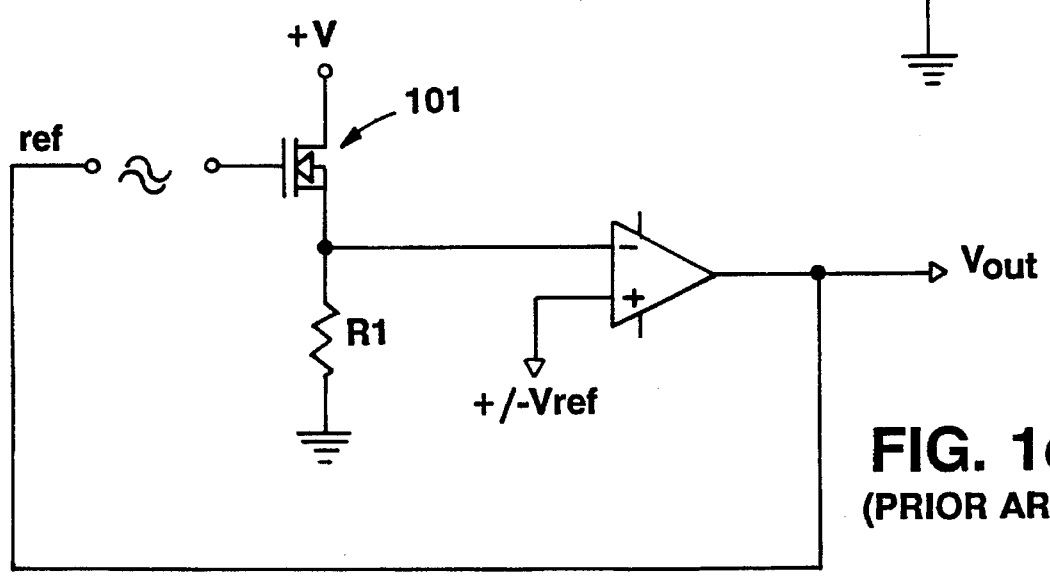
FIG. 1C is an electrical schematic diagram of a prior art common drain amplifier circuit in which both the voltage between the drain and the source, and the drain current, are held constant over time.
Figure 2:
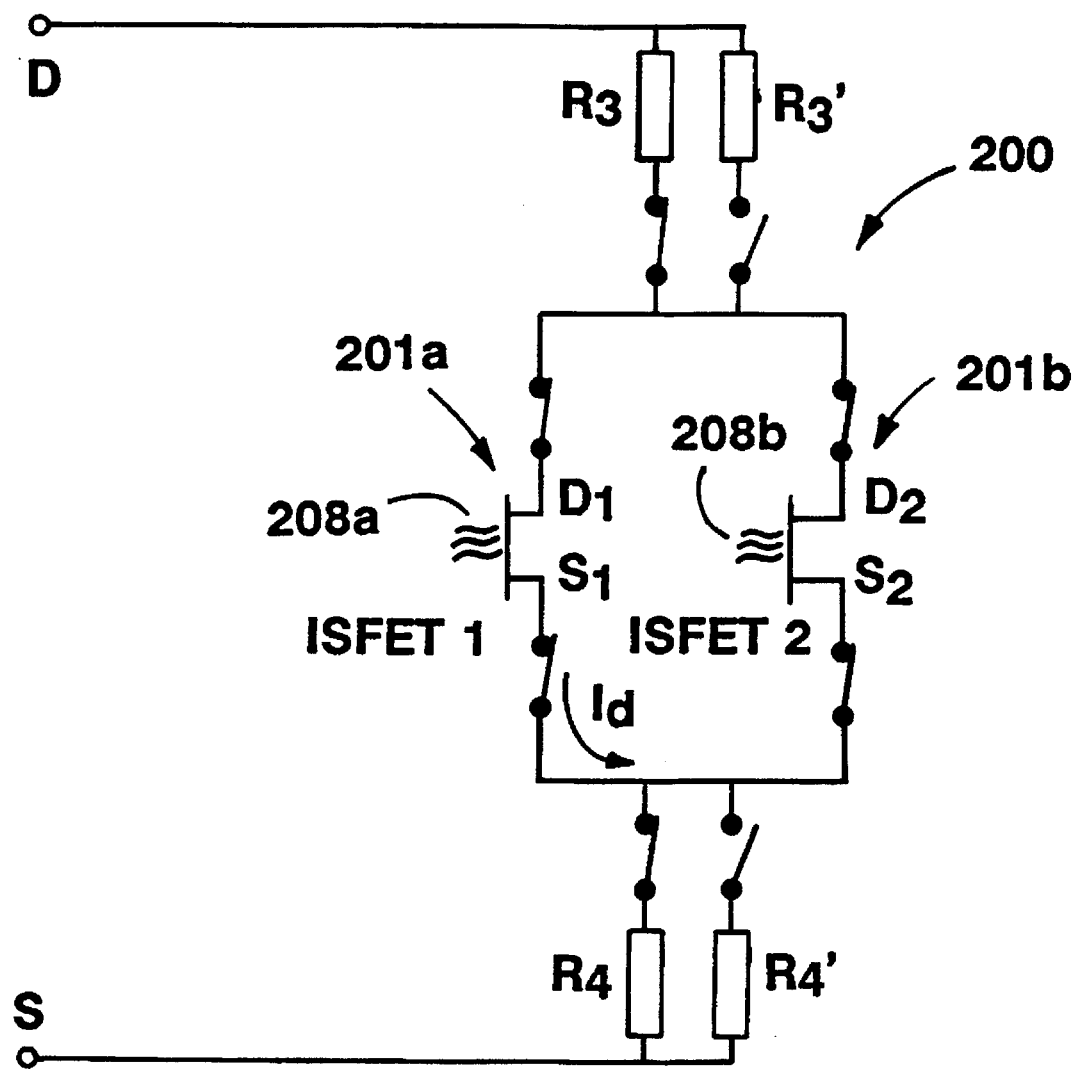
FIG. 2 is an electrical schematic diagram of a prior art circuit for multiplexing a plurality of ISFETs.
Figure 3:
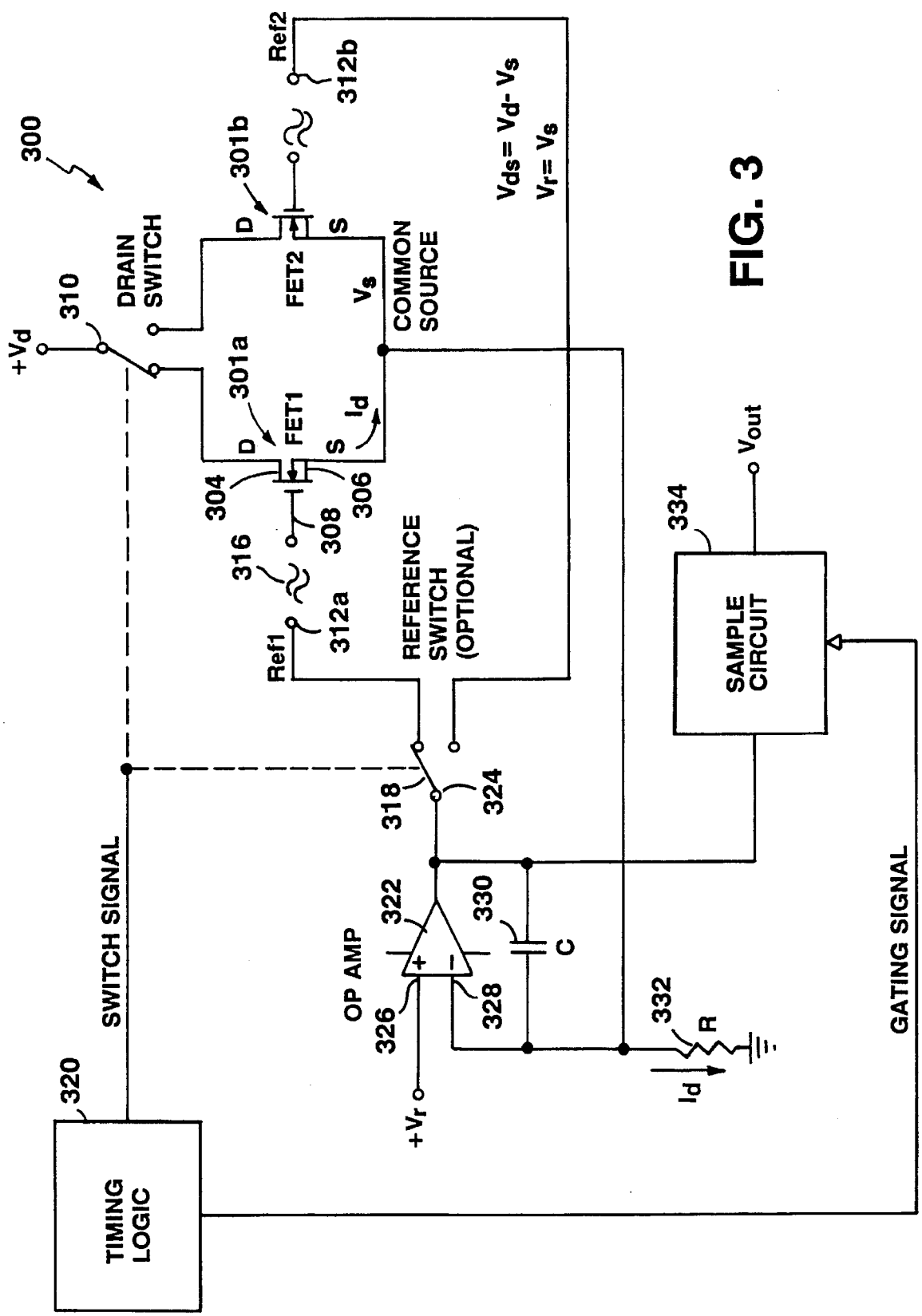
FIG. 3 is an electrical schematic diagram of the inventive circuit for multiplexing a plurality of ISFETs.

FIG. 3 is an electrical schematic diagram of a multiplexing circuit for multiplexing devices which have a relatively long thermal time constant, such as an ISFET multiplexing circuit 300, in accordance with the present invention. Two ISFETs 301a, 301b are shown for illustrative purposes. However, the present invention can accommodate any number of additional devices 301. Each ISFET 301 is configured in a common drain circuit. Since each ISFET 301 operates identically, the following description is limited to only one of the ISFETs 301 for the sake of brevity, but applies equally to each.

Each ISFET 301 has a drain 304, a source 306, and a gate 308. In the preferred embodiment of the present invention, the drain 304 is coupled to a drain voltage $V_d$ supply through a drain switch 310. The drain voltage supply outputs a generally stable voltage. The drain switch 310 is preferably a monolithic CMOS, single-pole, multi-throw type, the number of throws being equal to the number of ISFETs 301. Such switches are available from Motorola, Inc. (part no. MC14051B). However, any device may be used that can selectively couple the drain of each ISFET 301 with the drain voltage supply $V_d$ with a relatively short transition time with respect to the sample rate. In the preferred embodiment, the sample rate is such that each ISFET 301 is to be sampled at least once per second.

The drain switch 310 selectively couples the drain of each ISFET 301 to the voltage supply $V_d$ such that the drain 304 of only one ISFET 301 is coupled to the voltage supply $V_d$ at any one time. Each ISFET 301 is placed in contact with a solution 316, the properties of which are to be measured, causing an ion selective membrane which covers the gate 308 of the ISFET 301 to come into contact with the solution 316. At least one reference electrode 312 is also placed in contact with the solution 316. In the preferred embodiment of the present invention, a plurality of reference electrodes 312 are coupled to the output of a control means, such as an operational amplifier (op-amp) 322. If each of the ISFETs 301 are in contact with the same solution, a single reference electrode 312 may be used.

In an alternative embodiment of the present invention, the reference electrode 312 is coupled to a reference switch 318. The reference switch 318 is a monolithic CMOS, single-pole, multi-throw switch, similar to the drain switch 310, having a number of throw positions equal to the number of reference electrodes 312. The common contact 324 of the reference switch 318 is coupled to the output of the op-amp 322. Thus, the reference switch 318 allows the output of the op-amp 322 to be coupled to each of the reference electrodes 312 while maintaining isolation between each reference electrode 312. In another alternative embodiment, a single reference electrode 312 may be associated with more than one, but less than all, of the ISFETs 301.

Referring again to FIG. 3, the output of the op-amp 322 is also coupled to one side of a capacitor 330 and to a sample circuit 334. The inverting input 328 to the op-amp 322 is coupled to the source 306 of each ISFET 301, to the other side of the capacitor 330, and to one side of a current-limiting resistor 332. The other side of resistor 332 is connected to ground. The capacitor 330 provides a high frequency, negative feedback path which causes the gain of the op-amp 322 to "roll-off" at high frequency.

When an ISFET 301 is disconnected from the drain voltage supply $V_d$, no current flows through that ISFET 301, since the input impedance of its gate 308 (i.e., the impedance from the reference electrode 312 to drain 304 or source 306) is ideally infinite. For the purpose of this analysis, each ISFET 301 is considered to have an ideal input impedance. The ISFET 301 that is conducting (i.e., coupled to the drain voltage supply $V_d$ by the drain switch 310) is in the feedback path of the op-amp 322. The op-amp 322 maintains a constant drain current $I_d$ and drain-to-source voltage $V_{ds}$ by adjusting the voltage applied to the reference electrode 312. Drain current $I_d$ flows from the drain voltage supply $V_d$, through the conducting ISFET 301 from its drain 304 to its source 306, and down through the resistor 332 to ground.

The voltage at the inverting input to the op-amp 322 is equal to the drain current $I_d$ times the resistance R of the resistor 332. The non-inverting input 326 to the op-amp 322 is coupled to a reference voltage supply $V_r$. The reference voltage $V_r$ is lower than the voltage at the drain voltage supply $V_d$ and higher than ground.

The output of the op-amp 322 is equal to the difference between the voltage at the inverting and non-inverting inputs 328, 326 of the op-amp 322, multiplied by the gain of the op-amp 322 (which is ideally infinite at low frequency). The output of the op-amp 322 is coupled to the reference electrode 312 associated with the conducting ISFET 301, either directly or through the optional reference switch 318. The voltage at the reference electrode 312 biases the gate 308 of the conducting ISFET 301, thereby causing the drain current $I_d$ to increase with increased voltage on the reference electrode, and to decrease with decreased voltage on the reference electrode 312. The effect of this feedback loop is to hold the drain current $I_d$, and the drain-to-source voltage $V_{ds}$ essentially constant. In the preferred embodiment of the present invention, the drain current $I_d$ is approximately 25–200 microamps. The drain-to-source voltage $V_{ds}$ is approximately 0.5 to 2.5 volts. The closed loop bandwidth of the op-amp 322 is sufficiently greater than the bandwidth of the multiplex rate to ensure that the high frequency roll-off does not interfere with the response of the op-amp 322 at the multiplexing rate. The open loop bandwidth and slew rate of the op-amp 322 is high enough so that the feedback loop can close and settle to its new value without producing excessive transients which may damage any of the ISFETs 301.

The timing logic circuit 320 sends a switch signal to the drain switch 310 (and the reference switch 318, if present) to cause the drain 304 of a selected ISFET 301 to be coupled to the drain voltage supply $V_d$ (and, if the reference switch 318 is present, the reference electrode 312 to be coupled to the output of the op-amp 322). A predetermined time later, the timing circuit 320 sends a gating signal to the sample circuit 334 to cause the sample circuit 334 to sample the output of the op-amp 322. The sample time (time required to acquire the sample) is short relative to the thermal time constant of the selected ISFET 301. Upon securing the sample, the timing logic circuit 320 sends a switch signal to the drain switch 310 to couple a next ISFET 301 to the drain supply voltage $V_d$ (and to the reference switch 318 to couple the op-amp 322 to the reference electrode associated with the next ISFET 301). A predetermined time later, the timing circuit 320 sends a gating signal to the sample circuit 334 to again cause the sample circuit 334 to sample the output of the op-amp 322. This multiplexing process is repeated at a constant duty cycle for each ISFET 301 in the circuit.

Each output from the sample circuit 334 is sent to a processing and output circuit. The processing circuit demultiplexes the outputs from sample circuit 334 in known fashion. The processing circuit also provides compensation for the ambient temperature of the solution 316 and for the known characteristics of the particular ISFETs 301. A display circuit displays the results to the user in units appropriate to the characteristic being measured.

FUNCTIONAL DESCRIPTION

For the purpose of this explanation, the offset voltage of the reference electrode 312 is assumed to be constant and zero. Since the drain current $I_d$ and the drain-to-source voltage $V_{ds}$ of the conducting ISFET are held constant, the only variables in the circuit are the electro-chemical potential generated at the gate 308 of the conducting ISFET 301, the output of the op-amp 322 applied to the reference electrode 312, and the temperature of the ISFET 301. The temperature of the ISFET 301 is a function of the duration of the period of conduction, the amount of time between periods of conduction, and the ambient temperature of the solution 316. The temperature at any given point in time relative to the beginning of a period of conduction is essentially equal to the temperature at any other point in time equally distant from the beginning of a period of conduction, assuming the time between each period of conduction is the same. Also the system must have been operating long enough to reach thermal equilibrium (i.e., the rise in the temperature of each ISFET due to conduction is equal to the fall in temperature during the period between periods of conduction (see FIGS. 4A and 4B)). The ambient temperature can be measured by means of, for example, a thermistor or thermocouple. By compensating for the ambient temperature of the solution 316, controlling the duration of the period of conduction, sampling the output of the op-amp 322 at a precise moment relative to the beginning of each period of conduction, and controlling the amount of time between periods of conduction, each output voltage at each sample time is essentially equal to the output voltage of each other sample time for a particular state of the solution 316. The absolute time between the beginning of the period of conduction and the taking of the sample is irrelevant, provided (1) the time between the beginning of the period of conduction and the taking of the sample is constant from period to period, and (2) the time between periods of conduction is also constant from period to period. Therefore, samples may be taken at a very rapid rate. Each sample is an instantaneous reading of the state of the solution 316.

Figure 4A:
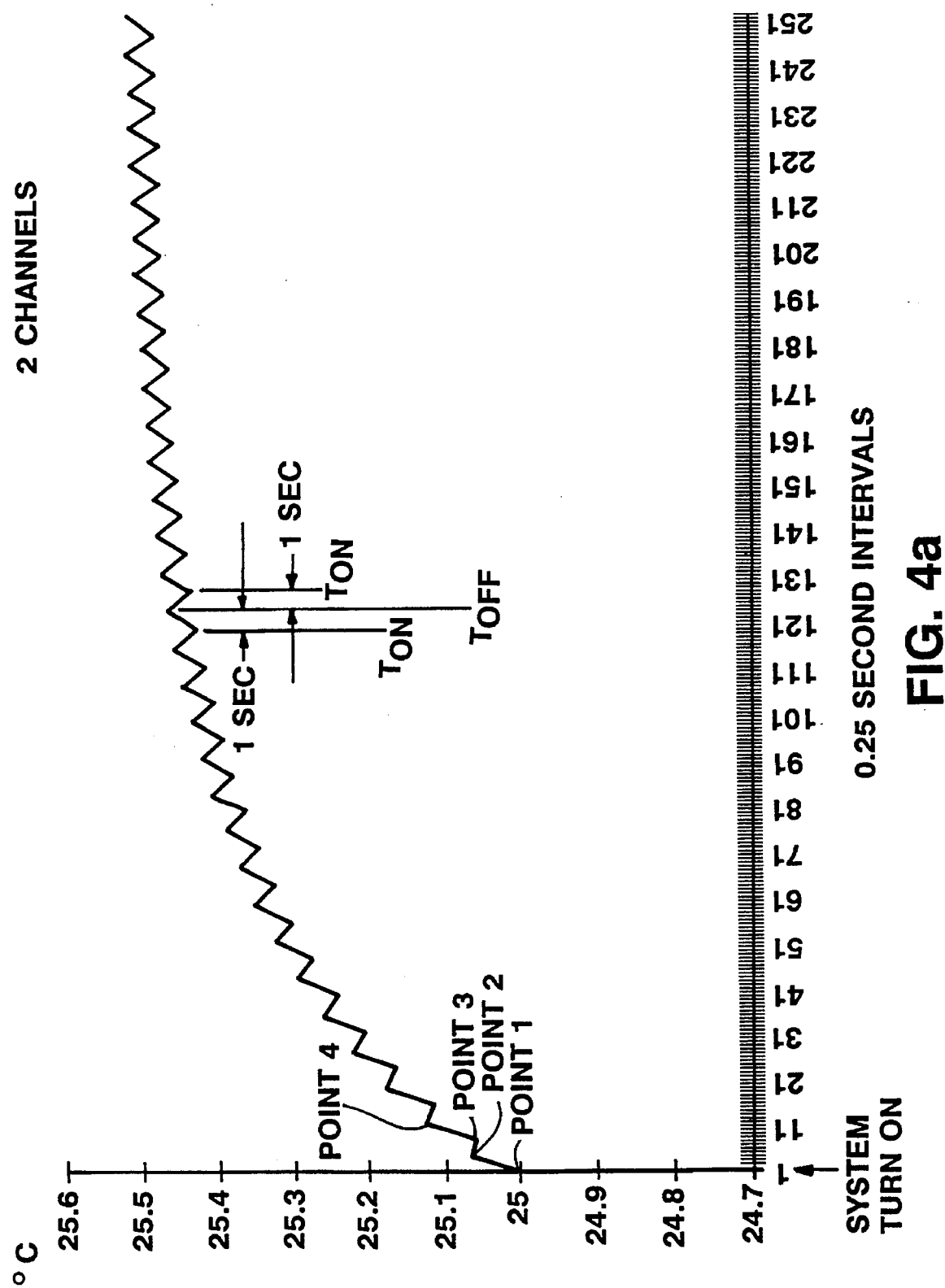
FIG. 4A is a graphical representation of the turn-on temperature stabilization of an ISFET of the inventive circuit in which two ISFETs are multiplexed verses time.
Figure 4B:
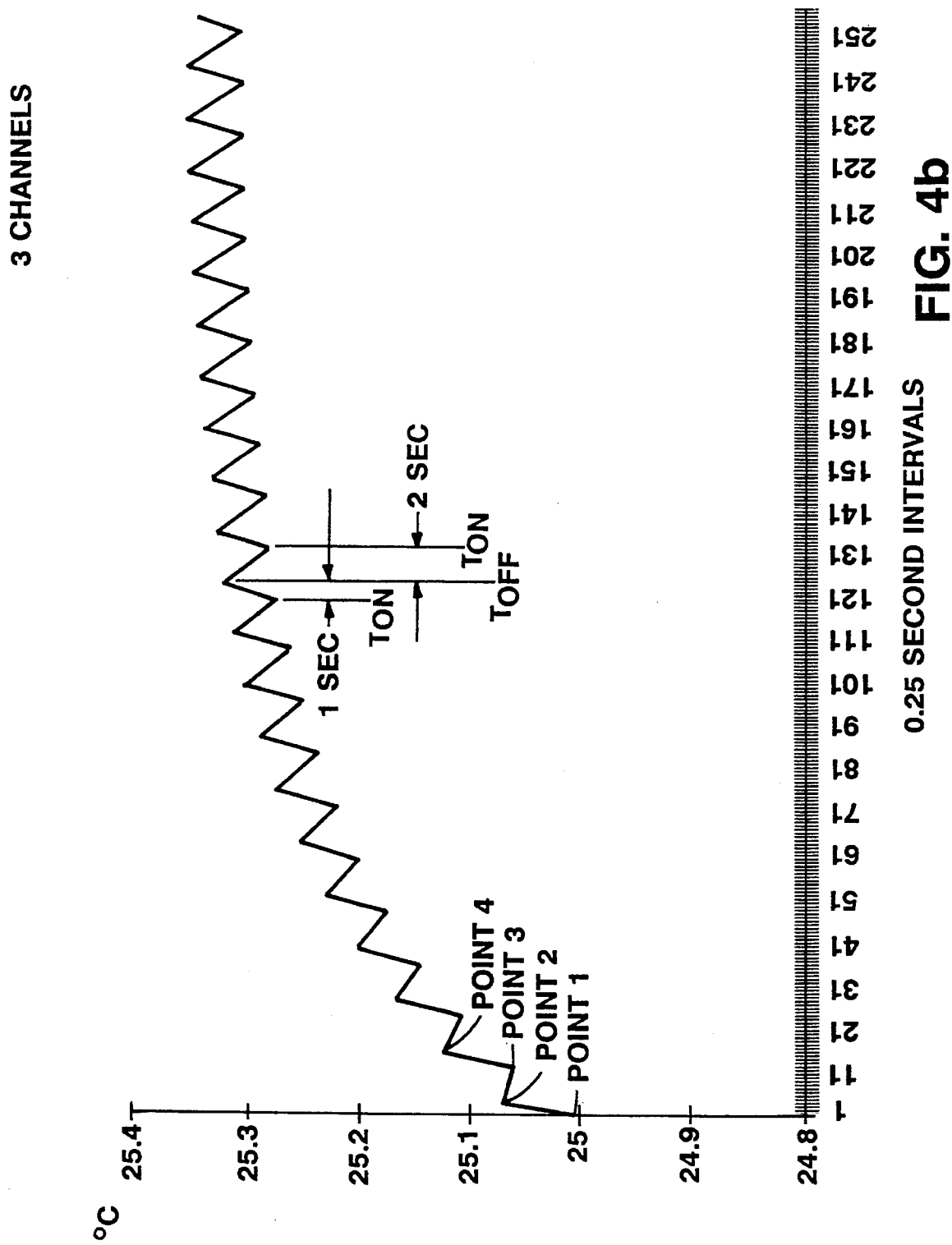
FIG. 4B is a graphical representation of the turn-on temperature stabilization of an ISFET of the present inventive circuit in which three ISFETs are multiplexed verses time.

FIGS. 4A illustrates the change in temperature over time of an ISFET 301 of the present inventive circuit in which two ISFETs are multiplexed. In the inventive system, each time $T_{on}$ that the ISFET 301 is conducting (i.e., that the time constant has been initiated), the temperature begins to rise exponentially as a function of time and drain current $I_d$. In the case illustrated in FIG. 4A, the conduction period is of the same duration as the interval between periods of conduction. In FIG. 4B, three ISFETs are multiplexed. Therefore, the period of conduction is only one half as long as the interval between periods of conduction (i.e., each ISFET is conducting for one third of each duty cycle). Since in the preferred embodiment of the present invention, $I_d$ is held constant and the interval is constant between the beginning of a period of conduction and the time a sample is taken, the temperature rise from the time the ISFET is turned on until a sample is taken is dependent only upon the temperature of the ISFET at the start of the conduction period. Unlike the circuits of the prior art, immediately after each of the sample times $T_s$, the ISFET 301 ceases conducting and begins to cool. When the ISFET is at relatively lower temperatures, the increase in temperature during a period of conduction is greater than the decrease in temperature during the time between periods of conduction. However, as the temperature of the ISFET at the start of each period of conduction increases, the difference between the amount of temperature rise and the amount of the temperature fall becomes less and less. A relatively short time after the system begins operating, the rise in the temperature of the ISFET that occurs during the period of conduction equals the fall in the temperature that occurs between periods of conduction. Once this occurs, the temperature of the ISFET is the same at the beginning of each period of conduction, and thus at each sample time. It can be seen that the temperature may be changing, even as each sample is being taken. Nevertheless, the average induced temperature at each sample time $T_s$ is equal to the average induced temperature at each other sample time $T_s$. Therefore, the output of the multiplexer circuit 300 of FIG. 3 can be calibrated to compensate for that average induced temperature.

In summary, the invention provides a circuit for multiplexing a plurality of devices having long stabilization time constants. The circuit includes a means for selectively initiating the time constant of each of the plurality of devices and a means for generating a sampling window a predetermined time after the time constant of each of the plurality of devices has been initiated. The output of the device of which the time constant has been initiated can be sampled during the sampling window.

A number of embodiments of the present invention have been described. Nevertheless, it will be understood that various modifications may be made without departing from the spirit and scope of the invention. For example, any amplifier configuration which maintains an approximately constant drain current $I_d$ and drain-to-source voltage $V_{ds}$ may be used. Furthermore, the timing logic circuit 320 and sample circuit 334 may be a digital computer, discrete digital logic, analog logic, or any other control and sampling means. Also, rather than using a drain switch 310, any means for interrupting the drain current $I_d$ may be used such that only one ISFET 301 is conducting at any one time, such as a source switch coupled between the source of each ISFET 301 and the capacitor 330, resistor 332, and op-amp 322, to interrupt the current $I_d$. Furthermore, the inventive circuit is not limited to use with ISFETs only, and may be used with any device which has a long stabilization time constant. Accordingly, it is to be understood that the invention is not to be limited by the specific illustrated embodiment, but only by the scope of the appended claims.

I claim:

1. A circuit for rapidly multiplexing a plurality of devices, each having an output proportional to an applied voltage and having a longer thermal stabilization time constant than the duration of a multiplexing cycle, including:

(a) means for sequentially initiating the time constant of each of the plurality of devices;

(b) means for generating a sampling window (1) a predetermined time after the time constant of each of the plurality of devices has been initiated, during which the output of the device of which the time constant has been initiated can be sampled, and (2) before stabilization of the thermal time constant;

wherein a duty cycle and the duration of each multiplexing cycle are essentially constant for each device.

2. The device circuit of claim 1, wherein the time between the end of a period of conduction by any of the devices and the beginning of a subsequent period of conduction by that device is such that each device conducts the drain current for a period of conduction having a predetermined duration, and ceases conducting the drain current for a predetermined amount of time between periods of conduction.

3. The device circuit of claim 1, further including at least one reference electrode means, each reference electrode means being coupled to a corresponding device, and to the amplifier means, for biasing the gate of the device.

4. The device circuit of claim 3, in which one or more of the reference electrode means are coupled to more than one device.

5. The device circuit of claim 3 or 4, further including a reference switch means, coupled between the amplifier means and each reference electrode means, and coupled to the timing means, for selectively coupling one or more electrode means to the amplifier means under the control of the timing means.

6. An ion-sensitive field effect transistor (ISFET) multiplexing circuit having a plurality of ISFETs, including:
   (a) control means, coupled to each ISFET, for maintaining a constant drain current through each ISFET and a constant drain-to-source voltage across each ISFET when such ISFET is in a current conducting state;
   (b) switch means, coupled to each ISFET, for sequentially allowing each ISFET to conduct current for an essentially constant predetermined period of conduction at essentially constant intervals, such that only one ISFET conducts current at any one time; and
   (c) sample means, coupled to the control means, for generating a sampling window a predetermined time after the beginning of a period of conduction to allow rapid multiplexing of the plurality of ISFETs before stabilization of the output of each ISFET.

7. An ion-sensitive field effect transistor (ISFET) circuit, including:
   (a) a plurality of ISFETs, each having an output proportional to an applied voltage and an input;
   (b) amplifier means, coupled to the input and output of each ISFET, for maintaining a constant drain current through each of the ISFETs, and a constant drain-to-source voltage across each ISFET, during periods of conduction by each such ISFET;
   (c) drain switch means, coupled between the drain of each ISFET and configured to be coupled to a drain voltage supply, for sequentially electrically coupling the drain voltage supply to the drain of each ISFET, such that only one ISFET is electrically coupled to the drain voltage supply at any one time;
   (d) timing means, coupled to the drain switch means, for controlling the timing of the drain switch means, such that the drain of each ISFET is coupled to the drain voltage supply for a predetermined period of conduction;
   (e) sample means, coupled to the amplifier means and to the timing means, for sampling the output of the amplifier means at a predetermined time within each period of conduction for rapidly multiplexing each ISFET in a cycle and sampling the output of each ISFET before the output has stabilized;
wherein a duty cycle and the duration of each multiplexing cycle are essentially constant for each ISFET.

8. The ISFET circuit of claim 7, wherein the time between the beginning of a period of conduction and the sampling of the amplifier means is a constant.

9. An ion-sensitive field effect transistor (ISFET) multiplexing circuit including:
   (a) a plurality of ISFETs, each having an output proportional to an applied voltage;
   (b) amplifier means, coupled to the output of each ISFET, for maintaining an essentially constant drain current through each ISFET, and an essentially constant drain-to-source voltage across each ISFET during a period of conduction;
   (c) drain voltage supply means for supplying an essentially stable voltage;
   (d) switch means, coupled to each ISFET for sequentially preventing the conduction of drain current in each ISFET;
   (e) timing means, coupled to the switch means, for controlling the timing of the switch, such that each ISFET conducts the drain current for a period of conduction having a predetermined duration, and ceases conducting the drain current for a predetermined amount of time between periods of conduction;
   (f) sample means, coupled to the amplifier means and to the timing means, for sampling the voltage at the output of the amplifier means at a predetermined time relative to the beginning of the period of conduction for rapidly multiplexing each ISFET in a cycle and sampling the output of each ISFET before the output has stabilized;
wherein a duty cycle and the duration of each multiplexing cycle are essentially constant for each ISFET.

10. An ion-sensitive field effect transistor (ISFET) multiplexing circuit having a plurality of ISFETs, each having an output proportional to an applied voltage, including:
   (a) an amplifier, coupled to each ISFET, for maintaining a constant drain current through each ISFET and a constant drain-to-source voltage across each ISFET when such ISFET is in a conducting state;
   (b) a switch, coupled to each ISFET, for selectively allowing each ISFET to conduct current for a predetermined period of conduction, such that only one ISFET conducts current at any one time; and
   (c) a sample circuit, coupled to the amplifier, for generating a sampling window a predetermined time after the beginning of a period of conduction for rapidly multiplexing each ISFET in a cycle and sampling the output of each ISFET before the output has stabilized;
wherein a duty cycle and the duration of each multiplexing cycle are essentially constant for each ISFET.

11. An ion-sensitive field effect transistor (ISFET) circuit, including:
   (a) a plurality of ISFETs, each having an output proportional to an applied voltage and an input;
   (b) an amplifier, coupled to the input and output of each ISFET, for maintaining a constant drain current through each of the ISFETs, and a constant drain-to-source voltage across each ISFET, during periods of conduction by each such ISFET;
   (c) a drain switch, coupled between the drain of each ISFET and configured to be coupled to a drain voltage supply, for selectively electrically coupling the drain voltage supply to the drain of each ISFET, such that only one ISFET is electrically coupled to the drain voltage supply at any one time;
   (d) a timing circuit, coupled to the drain switch, for controlling the timing of the drain switch, such that the drain of each ISFET is coupled to the drain voltage supply for a predetermined period of conduction;
   (e) a sample circuit, coupled to the amplifier and to the timing circuit, for sampling the output of the amplifier at a predetermined time within each period of conduction for rapidly multiplexing each ISFET in a cycle and sampling the output of each ISFET before the output has stabilized;
wherein a duty cycle and the duration of each multiplexing cycle are essentially constant for each ISFET.

12. An ion-sensitive field effect transistor (ISFET) multiplexing circuit including:
   (a) a plurality of ISFETs, each having an output proportional to an applied voltage and an input;
   (b) an amplifier, coupled to the input and output of each ISFET, for maintaining an essentially constant drain current through each ISFET, and an essentially constant drain-to-source voltage across each ISFET during a period of conduction by each ISFET;

(c) a drain switch, coupled between the drain of each ISFET and configured to be coupled to a drain voltage supply, for selectively electrically coupling the drain voltage supply to the drain of each ISFET, such that only one ISFET is electrically coupled to the drain voltage supply at any one time;

(d) a timing circuit, coupled to the drain switch, for controlling the timing of the drain switch, such that the drain of each ISFET is coupled to the drain voltage supply for a predetermined period of conduction;

(e) a sample circuit, coupled to the amplifier and to the timing circuit, for sampling the output of the amplifier at a predetermined time within each period of conduction for rapidly multiplexing each ISFET in a cycle and sampling the output of each ISFET before the output has stabilized;

wherein a duty cycle and the duration of each multiplexing cycle are essentially constant for each ISFET.

13. A method for rapidly sampling a plurality of devices, each having an output proportional to an applied voltage, and each having a longer thermal long time constant than the duration of a multiplexing cycle, including the steps of:

(a) sequentially initiating the time constant of each of the plurality of devices at essentially constant intervals and for essentially constant durations;

(b) generating a sampling window (1) a predetermined time after the time constant of each of the plurality of devices has been initiated, during which the output of the device of which the time constant has been initiated can be sampled and (2) before stabilization of the thermal time constant;

wherein a duty cycle and the duration of each multiplexing cycle are essentially constant for each device.

14. A method for determining the characteristics of a solution using a plurality of ISFETs each having a longer thermal long time constant than the duration of a multiplexing cycle, including the steps of:

(a) sequentially allowing one of the plurality of ISFETs to conduct current at essentially constant intervals and for essentially constant durations;

(b) generating a sampling window (1) a predetermined time after such ISFET begins conducting the current during which the output of such ISFET can be sampled and (2) before stabilization of a thermal time constant characteristic of such ISFET; and (c) repeating steps (a) and (b) for each of the plurality of ISFETs;

wherein a duty cycle and the duration of each multiplexing cycle are essentially constant for each ISFET.

15. The method of claim 14, further including the steps of:

(a) repeating steps a, b, and c of claim 14; and (b) controlling the duration between the beginning of a period of conduction by any of the ISFETs and the beginning of a subsequent period of conduction by that ISFET.

16. The method of claim 14, further including the steps of:

(a) adjusting the voltage at the input to the conducting ISFET, such that the current through that ISFET and a drain-to-source voltage across that ISFET are maintained essentially constant.

17. The method of claim 16, wherein the duration of a period of conduction is insufficient to allow the temperature of the ISFET to stabilize.

* * * * *